US012564495B2

(12) United States Patent
Varadarajan et al.

(10) Patent No.: US 12,564,495 B2
(45) Date of Patent: Mar. 3, 2026

---

(54) STEMMED MODULAR IMPLANT SYSTEM

(71) Applicant: Zimmer, Inc., Warsaw, IN (US)

(72) Inventors: Ravikumar Varadarajan, Warsaw, IN (US); Caitlyn Sue Schmeiser, Cary, IL (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 18/775,615

(22) Filed: Jul. 17, 2024

(65) Prior Publication Data

US 2025/0025305 A1 Jan. 23, 2025

Related U.S. Application Data

(60) Provisional application No. 63/527,731, filed on Jul. 19, 2023.

(51) Int. Cl.
| | |
|---|---|
| *A61B 17/72* | (2006.01) |
| *A61F 2/30* | (2006.01) |
| *A61F 2/40* | (2006.01) |
| *A61B 17/56* | (2006.01) |

(52) U.S. Cl.
CPC .......... *A61F 2/30734* (2013.01); *A61B 17/72* (2013.01); *A61B 2017/564* (2013.01); *A61F 2002/30011* (2013.01); *A61F 2002/30387* (2013.01); *A61F 2002/30827* (2013.01); *A61F 2002/30884* (2013.01); *A61F 2002/30894* (2013.01); *A61F 2002/30899* (2013.01)

(58) Field of Classification Search
None
See application file for complete search history.

(56) References Cited

U.S. PATENT DOCUMENTS

| | | | | |
|---|---|---|---|---|
| 4,728,333 A | * | 3/1988 | Masse ................... | A61F 2/3662 623/23.28 |
| 4,790,852 A | * | 12/1988 | Noiles ................ | A61B 17/1668 623/23.46 |
| 5,100,407 A | * | 3/1992 | Conrad ................. | A61F 2/4684 606/79 |
| 5,358,526 A | * | 10/1994 | Tornier ................. | A61F 2/4014 623/19.14 |
| 5,549,706 A | * | 8/1996 | McCarthy ............... | A61F 2/367 623/23.28 |
| 5,766,261 A | * | 6/1998 | Neal ................... | A61B 17/1659 606/85 |

(Continued)

FOREIGN PATENT DOCUMENTS

| | | | | |
|---|---|---|---|---|
| CN | 114886619 A | * | 8/2022 | .......... A61F 2/3609 |
| EP | 1374803 A1 | * | 1/2004 | ......... A61F 2/30739 |

OTHER PUBLICATIONS

English Translation CN 114886619 (Year: 2022).*

*Primary Examiner* — Jan Christopher L Merene
(74) *Attorney, Agent, or Firm* — SCHWEGMAN LUNDBERG & WOESSNER, P.A.

(57) ABSTRACT

A stemmed implant system can include a stem component and an accessory component. The stemmed component can include a first portion adapted to be anchored within a medullary canal of a bone and a second portion including a mounting boss defining an inner coupling surface. The accessory component can define an outer coupling surface adapted to engage the inner coupling surface of the mounting boss of the stem component to secure the accessory component to the stem component.

16 Claims, 8 Drawing Sheets

(56) References Cited

U.S. PATENT DOCUMENTS

| | | | | |
|---|---|---|---|---|
| 5,860,982 | A * | 1/1999 | Ro | A61F 2/4684 |
| | | | | 606/102 |
| 7,641,698 | B1 * | 1/2010 | Gibbs | A61F 2/4637 |
| | | | | 623/22.15 |
| 2001/0037152 | A1 * | 11/2001 | Rockwood, Jr. | A61F 2/40 |
| | | | | 623/19.12 |
| 2003/0149486 | A1 * | 8/2003 | Huebner | A61F 2/4657 |
| | | | | 623/908 |
| 2004/0010319 | A1 * | 1/2004 | McTighe | A61F 2/30767 |
| | | | | 623/23.34 |
| 2007/0078516 | A1 * | 4/2007 | Emami | A61F 2/4014 |
| | | | | 623/19.12 |
| 2008/0281428 | A1 * | 11/2008 | Meyers | A61F 2/3607 |
| | | | | 623/20.35 |
| 2023/0033626 | A1 * | 2/2023 | Dalla Pria | A61F 2/30749 |
| 2024/0130862 | A1 * | 4/2024 | Kiritsis | A61B 17/06 |
| 2024/0238103 | A1 * | 7/2024 | Leonard | A61F 2/32 |

* cited by examiner

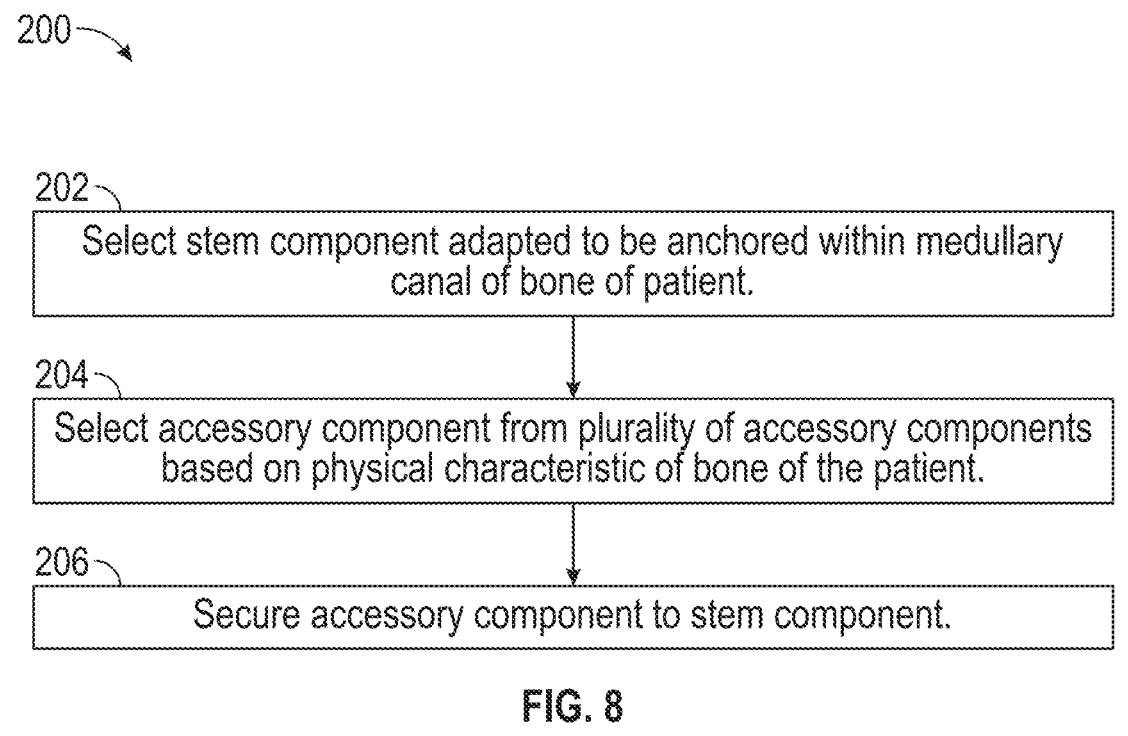

200

202

Select stem component adapted to be anchored within medullary canal of bone of patient.

204

Select accessory component from plurality of accessory components based on physical characteristic of bone of the patient.

206

Secure accessory component to stem component.

FIG. 8

STEMMED MODULAR IMPLANT SYSTEM

CLAIM OF PRIORITY

This application claims the benefit of U.S. Provisional Patent Application Ser. No. 63/527,731, filed on Jul. 19, 2023 the benefit of priority of which is claimed hereby, and which is incorporated by reference herein in its entirety.

TECHNICAL FIELD

This document pertains generally, but not by way of limitation, to stemmed prosthetic implants for use in arthroplasties (e.g., joint replacement procedures). More particularly, but not by way of limitation, this document pertains to a stemmed modular implant system including a plurality of removable accessory components for engaging proximal bone of a humerus or a femur.

BACKGROUND

In a natural shoulder joint (e.g., the glenohumeral joint), the proximal humerus includes a humeral head which articulates within the glenoid fossa of the scapula. Similarly, in a hip joint, the proximal femur includes a femoral head which articulates within the acetabular fossa of the pelvis. Over time, various ailments such as, among others, osteoarthritis, avascular necrosis, bone fractures, or bone resorption, can cause significant discomfort and diminish the functionality of a natural, or a replacement prosthetic, shoulder joint or hip joint of a patient. Such ailments often lead to surgical correction in the form of an arthroplasty, during which prosthetic components are implanted into the patient to help restore shoulder joint or hip joint functionality.

BRIEF DESCRIPTION OF THE DRAWINGS

FIG. 8 illustrates a method of adapting a modular implant system to a patient.

Figure 1:
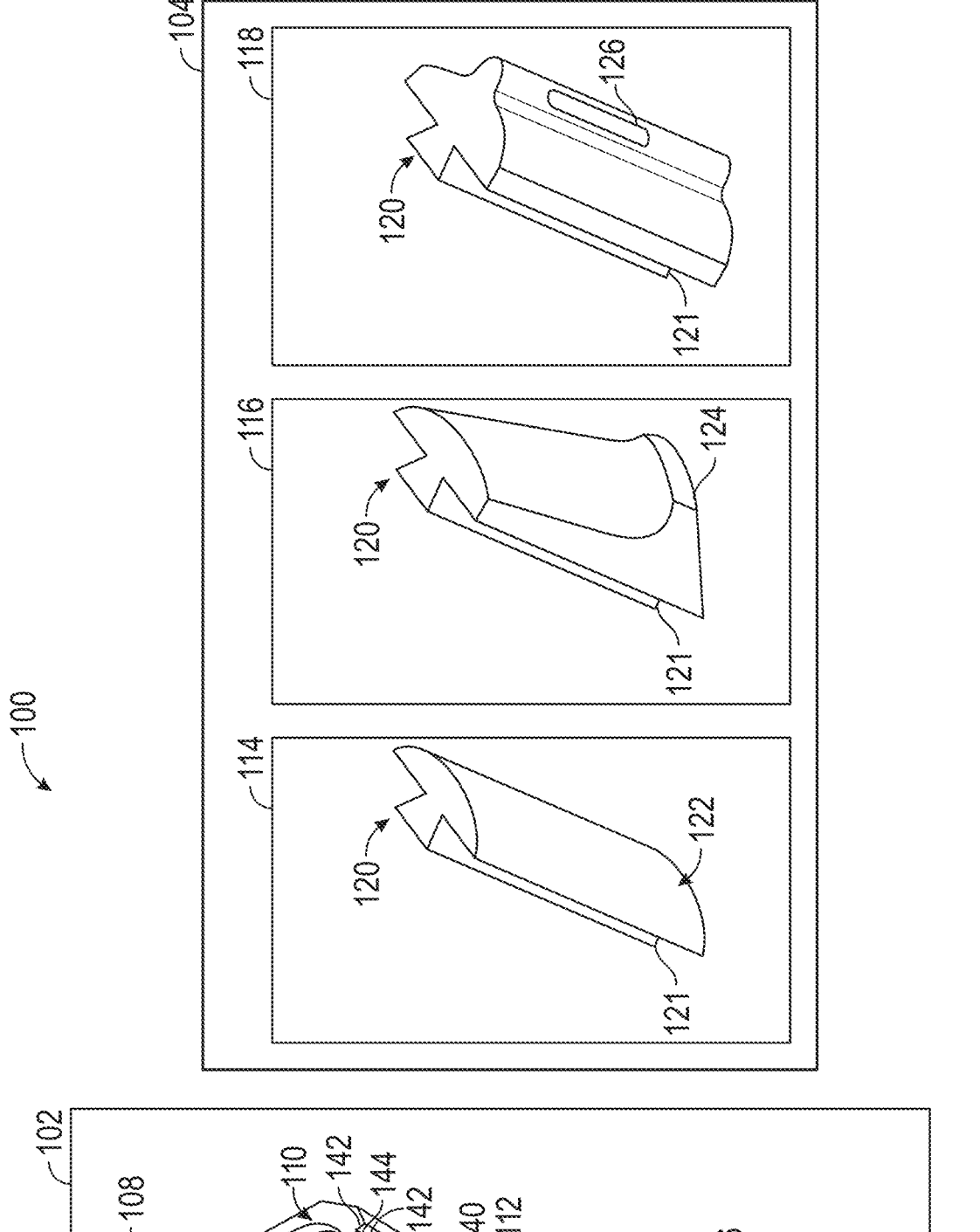
FIG. 1 illustrates an example stemmed modular implant system, in accordance with one or more embodiments of the present disclosure.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

A variety of stemmed prosthetic implants or implant systems for use in shoulder joint replacement (e.g., arthroplasty) procedures are presently available. Such implants or implant systems generally include an implantable stem component having a distal portion for anchoring within a diaphysis of a bone and a proximal portion for receiving a prosthetic component, such as a prosthetic humeral head or a cup for articulating against a prosthetic humeral head of a glenoid implant. However, while many aspects of stemmed implants have evolved over the years, such stemmed implants generally include universal, or otherwise minimally customizable, features for contacting and engaging cancellous or cortical bone of the proximal humerus. This can contribute to undesirable patient outcomes, such as by shielding proximal bone from the stress forces generated during normal joint movement, which often leads to postoperative periprosthetic bone loss (e.g., death or deterioration of bone in contact with or located near an implant).

Over time, periprosthetic bone loss can lead to failure of a replacement joint due to loosening of the fit between cancellous or cortical bone and a stemmed implant. Moreover, periprosthetic bone loss can make secondary arthroplasties performed to correct a failed replacement a complex procedure. For example, as a reduced amount of healthy bone is available for receiving a stemmed implant, or is otherwise available to secure a stemmed implant thereto, achieving strong fixation between a replacement stemmed component and healthy bone can be a difficult or challenging task. As a result, long-term survival rates of secondary arthroplasties performed to address implant loosening are generally much lower than long term-survival rates of primary, or initial, arthroplasties.

The present disclosure can help to address the above issues, among others, such as by providing a stemmed modular implant system. For example, the stemmed modular implant system can include a stem component defining an inner coupling surface and a plurality of accessory components each defining an outer coupling surface adapted to engage the inner coupling surface to secure any of the accessory components to the stem component. Each of the plurality of accessory components can be adapted to engage proximal bone, such as cortical or cancellous bone of a humerus or femur, to transfer stress forces there into or help secure one or more bone fragments there to. In view of the above, the stemmed modular implant system of the present disclosure can provide a number of benefits to both patients and surgeons. For example, the plurality of accessory components can allow a surgeon to select an accessory component to customize the stem component based on one or more physical characteristics of a patient's bone, such as including, among others, the size and shape of a patient's proximal humerus or femur, an amount of medial healthy bone remaining, or whether one or more bone displaced bone fragments are present.

This can improve the ability of the stem component to transfer stress forces into proximal bone to prevent stress shielding, to, in turn, prevent postoperative periprosthetic bone loss and thereby improve patient outcomes. Moreover, the uniform nature of the inner coupling surface and the outer coupling surface can enable a surgeon to pair one of a plurality of different stem components with one of a plurality of different accessory components. This can help to maintain a relatively low overall cost for a patient, such as by allowing a surgeon to customize a universally shaped stem component applicable to a wide variety of patients with a uniquely shaped accessory component applicable to an individual patient, or otherwise a lesser number of patients. In view of the above, the stemmed modular implant system can benefit both patients and surgeons by providing a higher level of customization relative to existing implantable stemmed components.

FIG. 1 illustrates an example stemmed modular implant system 100. The stemmed modular implant system 100 can include a stem component 102 and a plurality of accessory components 104. The stem component 102 can include a first portion 106 and a second portion 108. The first portion 106 can be adapted to be inserted into, and anchored within, a diaphysis of a bone. For example, the first portion 106 can be sized and shaped to be cemented or press-fit within a medullary canal of a bone, such as a diaphysis of a humerus or a femur. In some examples, the first portion 106 can be universally sized and shaped. In other examples, the stemmed modular implant system 100 can include a plurality of individual stem components, such as, but not limited to, between two and twenty uniquely configured stem components to thereby form a standardized range of sizes and shapes (e.g., different longitudinal lengths, outer diameters, or taper angles) for the first portion 106.

This can enable a surgeon to conveniently select the stem component 102 therefrom based on one or more physical characteristics of a patient's bone including, but not limited to, the natural size and shape of the patient's medullary canal or a type of arthroplasty to be performed. The second portion 108 can include a mounting boss 110. The mounting boss 110 can generally be an outermost portion, and can define an outer circumference of, the second portion 108. The mounting boss 110 can be universally sized and shaped. In some examples, the mounting boss 110 can define a first end surface 111. The first end surface 111 can be a lowermost surface of the mounting boss 110, such as separating the first portion 106 from the second portion 108. In some examples, the first end surface 111 can define a greater circumference than a circumference defined by the first portion 106.

The mounting boss 110 of the second portion 108 can be adapted to receive any accessory component of the plurality of accessory components 104. For example, the mounting boss 110 can define an inner coupling surface 112. In some examples, such as shown in FIG. 1, the plurality of accessory components 104 can include a first accessory component 114, a second accessory component 116, and a third accessory component 118. Each accessory component of the plurality of accessory components 104 can define an outer coupling surface 120. The outer coupling surface 120 can be adapted to contact and engage the inner coupling surface 112 of the stem component 102 to secure any of the plurality of accessory components 104 to the stem component 102.

The plurality of accessory components 104 can allow a surgeon to customize the stemmed modular implant system 100 to be customized to the anatomy of a variety of individual patients to help prevent stress shielding of proximal medial bone. First, the first accessory component 114 can be adapted for and selected by a surgeon in a primary or an initial arthroplasty, such as where all, or a greater portion, of an epiphysis or a metaphysis of a patient's bone remains. For example, the first accessory component 114 can include an outer surface 122 adapted to contact and engage a first bone surface 132 (FIG. 2A) within a medial portion of a patient's proximal humerus to transfer stress forces generated during normal joint movement there into.

Second, the second accessory component 116 can be adapted for and selected by a surgeon in a secondary, such as a revision, arthroplasty where none of an epiphysis or a lesser portion or none of a metaphysis of a patient's bone remains. For example, the second accessory component 116 can include a projection 124 adapted to contact and engage a second bone surface 154 (FIGS. 3A & 4A) forming an uppermost end of a medial portion of a patient's proximal humerus, to transfer stress forces generated during normal joint movement there into. Third, the third accessory component 118 can be adapted for and selected by a surgeon in a secondary, such a fracture correction, arthroplasty, where one or more displaced bone fragments of a patient's bone are present. For example, the third accessory component 118 can define at least one aperture 126 or one or more grooves 127 (FIGS. 4B & 5A-5B) each adapted for receiving or retaining a suture or a suture anchor to provide a surgeon with various options for secured the one or more displaced bone fragments to the stem component 102 in anatomically accurate locations.

In the operation of some examples, a surgeon can obtain imaging data, such as computed topography (hereinafter "CT") data, of a shoulder joint of an individual patient. The imaging data can then be reviewed and analyzed to create a surgical plan. In some examples, the surgical plan can be created using a preoperative planning software, such the Signature™ ONE Surgical Planning System from Zimmer Biomet, Inc. of Warsaw, Indiana (hereinafter "Zimmer Biomet"). Next, a surgeon can then select the stem component 102 and one accessory component from the plurality of accessory components 104 based on the surgical plan. For example, the stem component 102, and one of the first accessory component 114, the second accessory component 116, or the third accessory component 118, can be selected based on one or more physical characteristics of the patient's bone, such as, but not limited to, the natural size and shape of a proximal humerus or femur, an amount of bone remaining in a medial portion of the proximal humerus or femur, such as after an amount of bone resorption or decay thereof, or whether the proximal humerus or femur includes one or more bone fractures or displaced bone fragments.

Finally, the surgeon can assemble the stemmed modular implant system 100 by securing the stem component 102 to a selected accessory component of the plurality of accessory components 104. For example, the surgeon can slide the outer coupling surface 120 of one of the plurality of accessory component 104 along the inner coupling surface 112 of the mounting boss 110 until the first end surface 111 of the mounting boss 110 is aligned with a second end surface 121 of one of plurality of accessory components 104. In view of the above, the stemmed modular implant system 100 can enable a proximal or otherwise upper portion of a stemmed humeral or femoral implant to be customized to the anatomy of individual patients to help prevent stress shielding of proximal medial bone and the periprosthetic bone loss associated therewith.

Figure 2B:
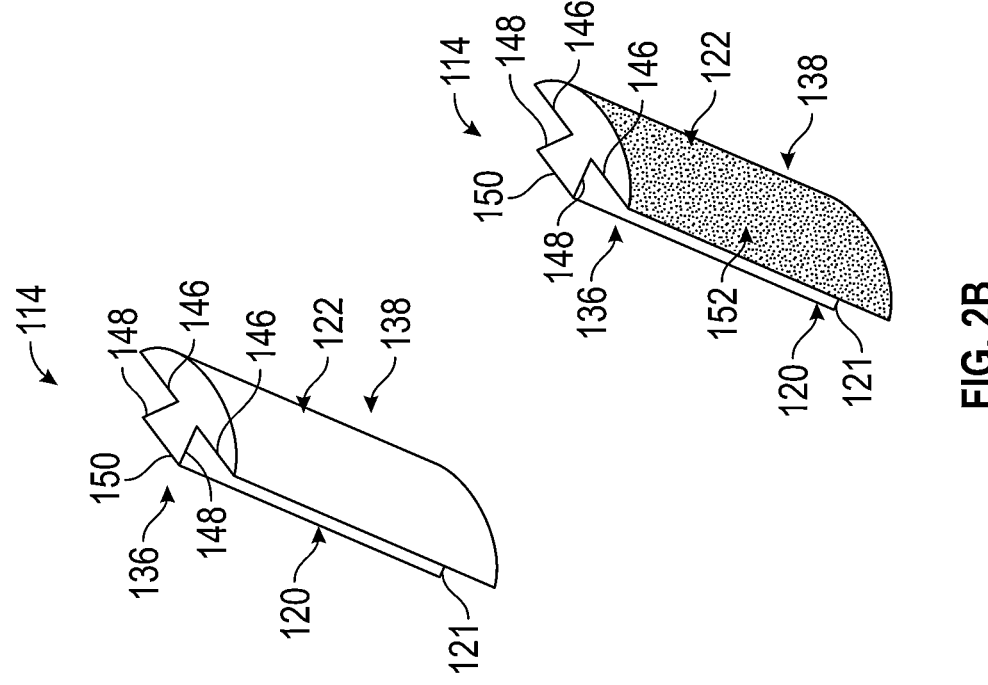
FIG. 2B illustrates two examples of a first accessory component, in accordance with one or more embodiments of the present disclosure.
Figure 2A:
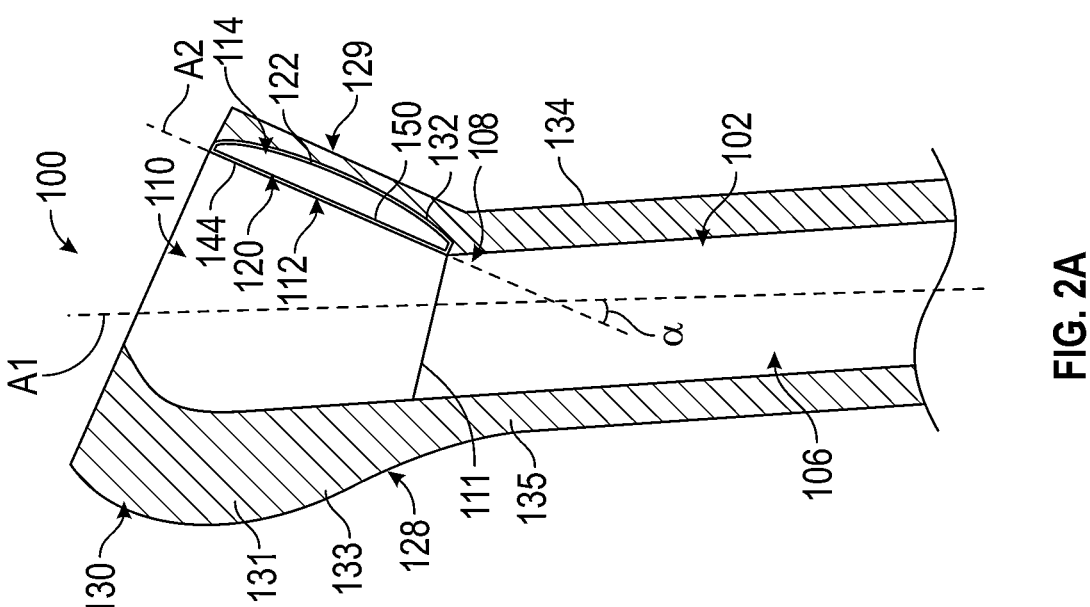
FIG. 2A illustrates a cross-section of an example stemmed modular implant system received within a proximal humerus, in accordance with one or more embodiments of the present disclosure.
Figure 3B:
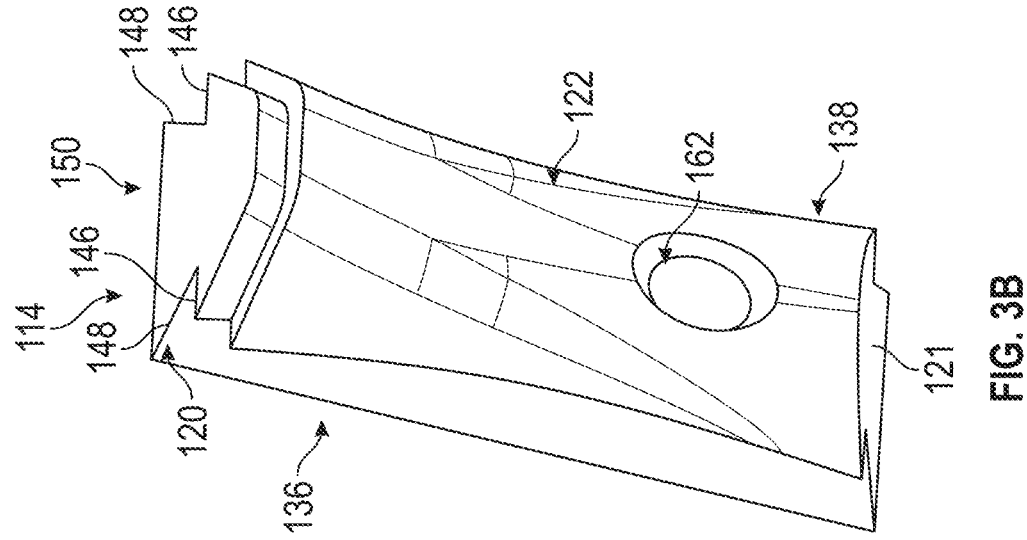
FIG. 3B illustrates an example first accessory component, in accordance with one or more embodiments of the present disclosure.
Figure 3A:
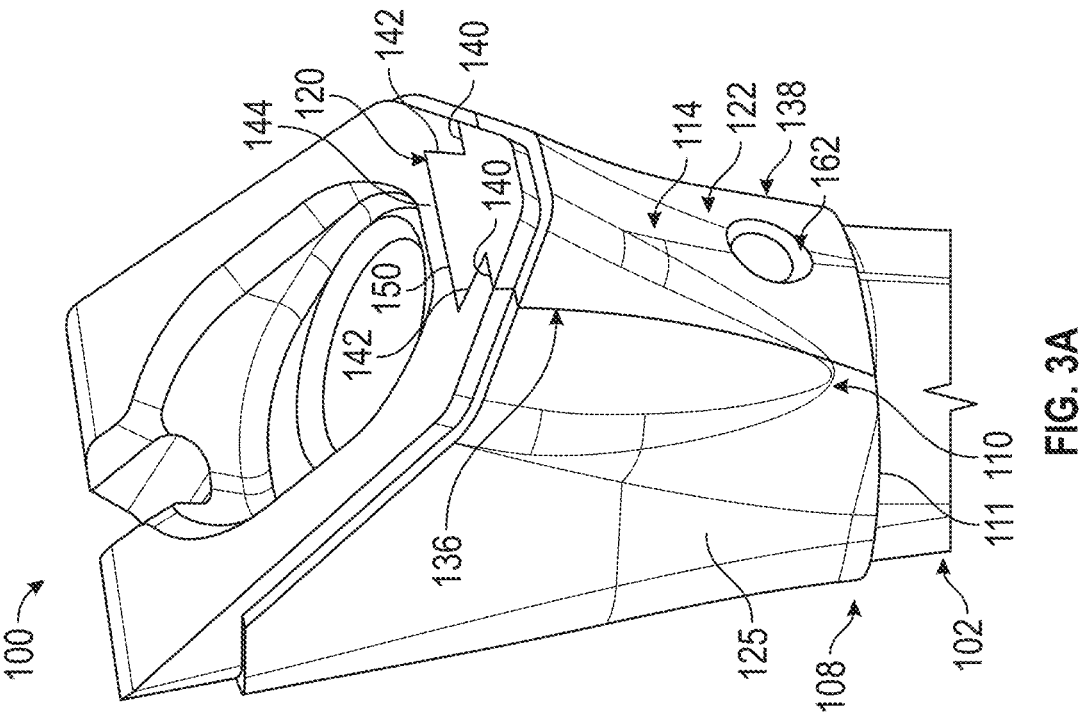
FIG. 3A illustrates an example stemmed modular implant system including a first accessory component, in accordance with one or more embodiments of the present disclosure.

FIG. 2A illustrates a cross-section of an example stemmed modular implant system 100 received within a proximal humerus 128, in accordance with one or more embodiments of the present disclosure. FIG. 2B illustrates two examples of a first accessory component 114, in accordance with one or more embodiments of the present disclosure. FIG. 3A illustrates a cross-section of an example stemmed modular implant system 100 including a first accessory component 114, in accordance with one or more embodiments of the present disclosure. FIG. 3B illustrates an example first accessory component 114, in accordance with one or more embodiments of the present disclosure. FIG. 2A-3B are discussed below concurrently. Also shown in FIG. 2A is a first axis A1 and a second axis A2.

As shown in FIG. 2A, the proximal humerus 128 can include a medial portion 129, a lateral portion 130, a first bone surface 132, and an outer bone surface 134. The medial portion 129 and the lateral portion 130 can generally be inner and outer portions, respectively, of the proximal humerus 128. For example, the medial portion 129 and the lateral portion 130 can be opposite radial segments, relative to first axis A1, of the stem component 102. The proximal humerus 128 can also include an epiphysis 131 (FIG. 2A), a metaphysis 133 (FIG. 2A), and a diaphysis 135 (FIG. 2A). The first bone surface 132 can define an anatomical void extending within the medial portion 129 through the epiphysis 131 into the metaphysis 133. Such an anatomical void can be formed, or otherwise, created to help prepare the medial portion 129 to receive the mounting boss 110 (FIG. 2A) and the second portion 108 (FIG. 2A) of the stem component 102 (FIG. 2A). The first bone surface 132 can depend on various factors, such as, but not limited to, the extent of bone loss or degradation of the medial portion 129 of the proximal humerus 128.

The stem component 102 (FIGS. 2A & 3A) can define the first axis A1. The first axis A1 can be a longitudinal axis of the stem component 102, such as extending centrally through the first portion 106 (FIG. 2A) and the second portion 108 (FIGS. 2A & 3A). The second axis A2 can be an axis defined by the inner coupling surface 112 (FIG. 2A) of the mounting boss 110 (FIGS. 2A & 3A). The mounting boss 110 can extend at various angles relative to the first portion 106 of the stem component 102. For example, an angle α (FIG. 2A) can be the angle formed at an intersection of the second axis A2 and the first axis A1. The angle α can measure between, but not limited to, about 20 degrees to about 60 degrees. In one example, such as shown in FIG. 2A, the angle α can be about 35 degrees. The first accessory component 114, as well as the second accessory component 116 (FIGS. 1, 4A-4B, & 5A-5B) and the third accessory component 118 (FIGS. 1, 5A-5B, & 6A-6B), can each include a medial portion 136 and a lateral portion 138. The medial portion 136 can include the outer coupling surface 120 and the second end surface 121. The second end surface 121 can be a lowermost end surface of the medial portion 136. The lateral portion 138 can include the outer surface 122. The outer surface 122 can be an outermost surface, such as defining an entire surface area of the lateral portion 138.

The outer surface 122 of the first accessory component 114 can form a generally planar or a flattened shape, or alternatively, a curved or otherwise semi-annular shape such as shown in FIGS. 2A-2B. In further examples, the outer surface 122, or one or more portions thereof, can define other three-dimensional shapes, such as shown in FIGS. 3A-3B. The outer surface 122 can be sized and shaped to extend flush with an outer stem surface 125 (FIG. 3A) defined by the mounting boss 110 of the stem component 102, such as shown in FIG. 3A, to replicate an unmodified, or otherwise stock surface, of a presently existing stem component not including the inner coupling surface 112. In other examples, the outer surface 122 can alternatively be sized and shaped to extend distally, radially, or otherwise outwardly beyond the outer stem surface 125 (FIG. 3A) of the mounting boss 110 of the stem component 102.

The inner coupling surface 112 and the outer coupling surface 120 can form complimentary or corresponding three-dimensional shapes, such as adapted to engage one another via a press fit. For example, the inner coupling surface 112 and the outer coupling surface 120 can form a dovetail joint there between. In such examples, the inner coupling surface 112 can include a first pair of contacting surfaces 140 (FIGS. 1 & 3A), a second pair of contacting surfaces 142 (FIGS. 1 & 3A), and a first contacting surface 144 (FIGS. 1, 2A, & 3A); and the outer coupling surface 120 can include a third pair of contacting surfaces 146 (FIGS. 2B & 3B), a fourth pair of contacting surfaces 148 (FIGS. 2B & 3B), and a second contacting surface 150. The first pair of contacting surfaces 140 can extend parallel to, and distally offset from, the first contacting surface 144; and the third pair of contacting surfaces 146 can extend parallel to, and distally offset from, the second contacting surface 150.

The second pair of contacting surfaces 142 and the fourth pair of contacting surfaces 148 can extend at various angles relative to the first pair of contacting surfaces 140 and the third pair of contacting surfaces 146, respectively. For example, each of the second pair of contacting surfaces 142 and the fourth pair of contacting surfaces 148 can extend at an angle of between, but not limited to, about 40 degrees to about 50 degrees, relative to each of the first pair of contacting surfaces 140 and the third pair of contacting surfaces 146, respectively. In one example, each of the second pair of contacting surfaces 142 and the fourth pair of contacting surfaces 148 can extend at an angle of 45 degrees relative to each of the first pair of contacting surfaces 140 and the third pair of contacting surfaces 146, respectively.

In additional examples, the inner coupling surface 112 and the outer coupling surface 120 can form complimentary or corresponding three-dimensional shapes adapted to engage one another via a taper fit. For example, the second pair of contacting surfaces 142 can form a male taper, such as by sloping toward each other near the first end surface 111, and the fourth pair of contacting surface 148 can form a corresponding female taper, such as by sloping away from each other near the second end surface 121. Alternatively, the second pair of contacting surfaces 142 can form a female taper, such as by sloping away from each other near the first end surface 111, and the fourth pair of contacting surfaces 148 can form a corresponding male taper, such as by sloping toward each other near the second end surface 121.

During the assembly of the stemmed modular implant system 100, the first pair of contacting surfaces 140 and the third pair of contacting surfaces 146, the second pair of contacting surfaces 142 and the fourth pair of contacting surfaces 148, and the first contacting surface 144 and the second contacting surface 150, can slide along one another until the outer coupling surface 120 is fully received within, or is otherwise fully seated on, the inner coupling surface 112. For example, the outer coupling surface 120 can be fully received within the inner coupling surface 112 when the first end surface 111 of the mounting boss 110 is aligned with the second end surface 121 of the medial portion 136. In view of the above, the surface contact or engagement between the inner coupling surface 112 and the outer coupling surface 120 can be sufficient to prevent relative movement of the first accessory component 114, the second accessory component 116, or the third accessory component 118 along the second axis A2.

In some examples, the lateral portion 138 of the first accessory component 114 can be based on a statistical bone model representing a calculated average size and shape of the medial portion 129 of the proximal humerus 128 or a proximal femur, or a calculated average size and shape of the first bone surface 132 within the medial portion 129, of plurality of different patients. For example, the size and shape of the outer surface 122, or other parameters or characteristics of the lateral portion 138, can be configured based on a statistical bone model. A statistical bone model can be generated, for example, from imaging data including, but not limited to, CT, X-ray, or Magnetic Resonance Imaging data. In one example, the Zimmer Biomet ZiBRA Bone Resection Atlas (hereinafter the "ZiBRA Atlas"), which includes imaging data representing aggregated bone morphology from a diverse global population, can be used to create such a statistical bone model.

In some examples, the stemmed modular implant system 100 can include a plurality of first accessory components, such as, but not limited to, two, three, four, or five uniquely configured first accessory components to thereby form a standardized range of different shapes and sizes for the outer surface 122 of the lateral portion 138. This can enable a surgeon to conveniently select the first accessory component 114 therefrom based on one or more physical characteristics of a patient's bone, such as the natural size and shape of the medial portion 129, an amount of the epiphysis 131 or the metaphysis 133 remaining within the medial portion 129, or the size and shape of the first bone surface 132. In a further example, the lateral portion 138 can be based on imaging data collected from an individual patient, such as to help enable the outer surface 122 of the lateral portion 138 engage abnormal humeral geometry falling outside a range of geometry a plurality of first accessory components is sized and shaped to engage. In such an example, it can be appreciated that the lateral portion 138 of the first accessory component 114 can be configured and manufactured specifically for the individual patient.

In some examples, the first accessory component 114 can include a porous surface 152 (FIG. 2B). For example, a portion, or all, of a surface area of the outer surface 122 can include the porous surface 152. The porous surface 152 can generally be a textured or a patterned three-dimensional structure adapted to help facilitate post-operative bone ingrowth and vascularization. In one example, the porous surface 152 can be realized using Zimmer Biomet OsseoTi® Porous Metal Technology, which uses human CT imaging data in combination with 3D printing technology to build a structure that mimics the architecture of human cancellous bone. In other examples, the porous surface 152 can be realized using Zimmer Biomet Proximal PPS® Porous Plasma Spray.

The first accessory component 114 can be adapted for and selected by a surgeon in primary, or initial, arthroplasties, such as where any portion of the epiphysis 131 within the medial portion 129, or about 100 percent to about 50 percent of the metaphysis 133 within the medial portion 129, remains. First, for example, the outer surface 122 can be sized and shaped to engage cancellous bone within the medial portion 129 by contacting and engaging the first bone surface 132 without penetrating cortical bone of the outer bone surface 134. In view of the above, when the stem component 102 and the first accessory component 114 are inserted into the proximal humerus 128, the outer surface 122 can engage a relatively large amount of surface area of cancellous bone within the medial portion 129. As such, the first accessory component 114 can enable the stem component 102 to effectively transfer stress forces generated during normal joint movement into the medial portion 129 to prevent stress-shielding thereof and the postoperative periprosthetic bone loss or resorption associated therewith.

Figure 4B:
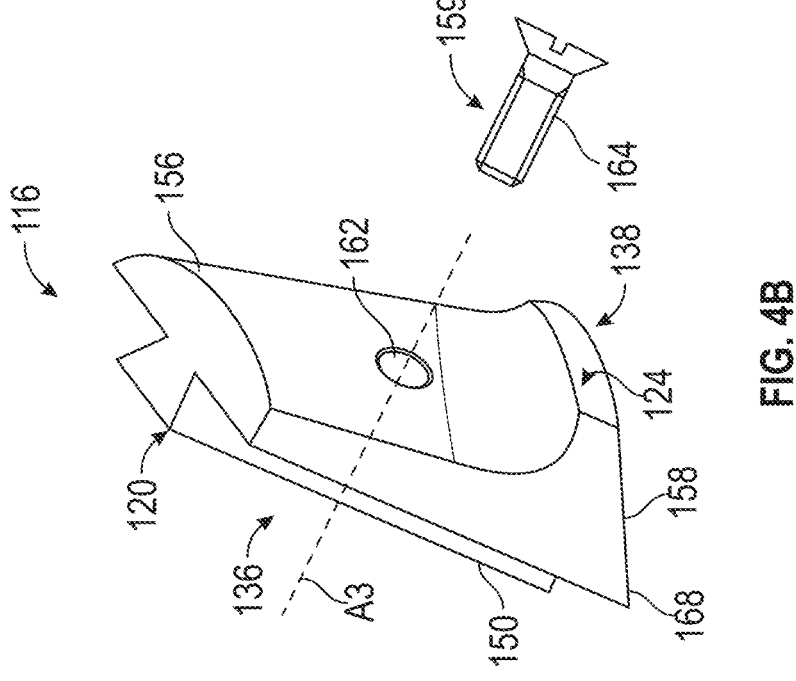
FIG. 4B illustrates an example second accessory component, in accordance with one or more examples of the present disclosure.
Figure 4A:
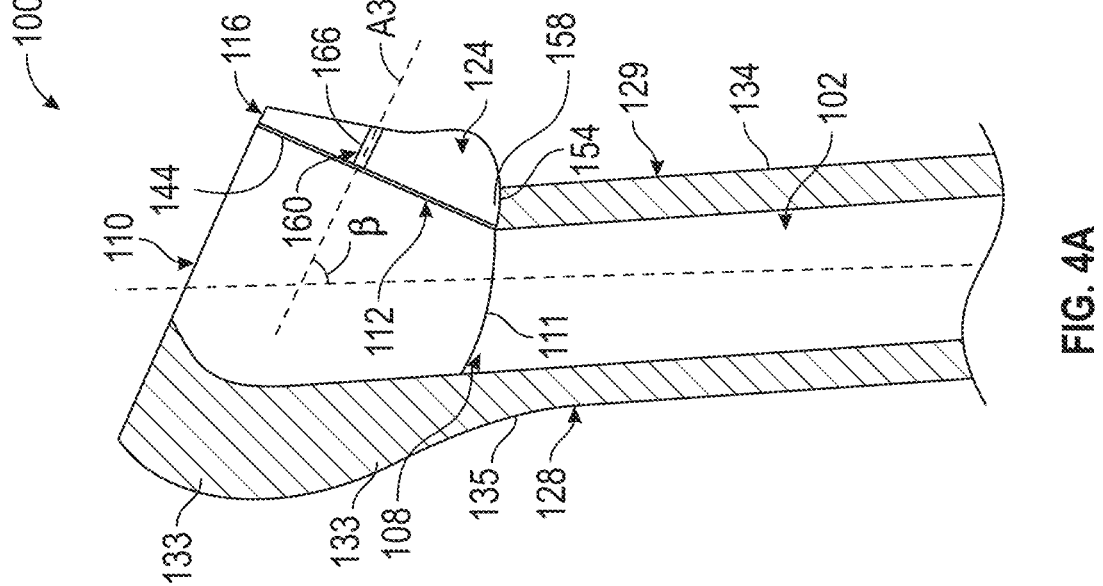
FIG. 4A illustrates a cross-section of an example stemmed modular implant system received within a proximal humerus.
Figure 5B:
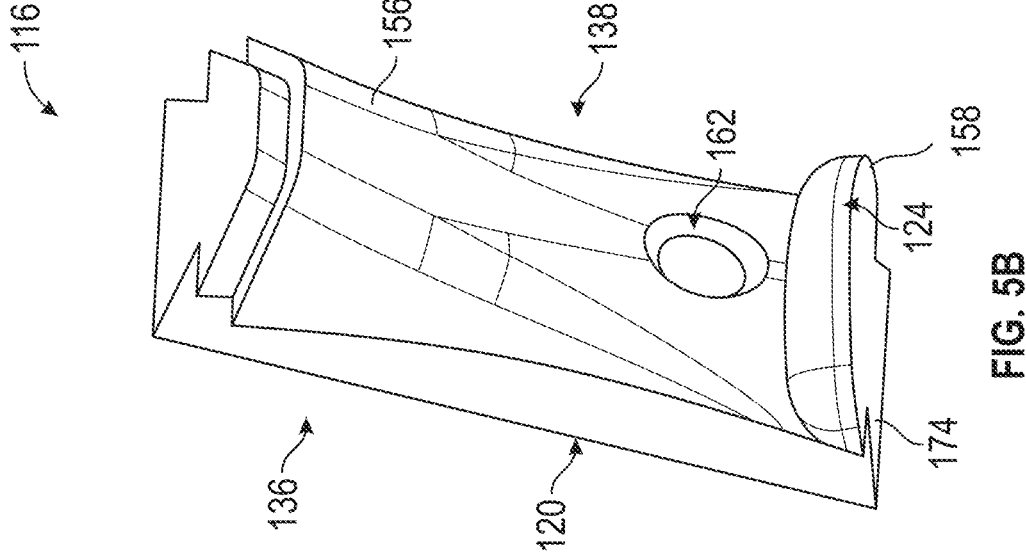
FIG. 5B illustrates an example second accessory component, in accordance with one or more examples of the present disclosure.
Figure 5A:
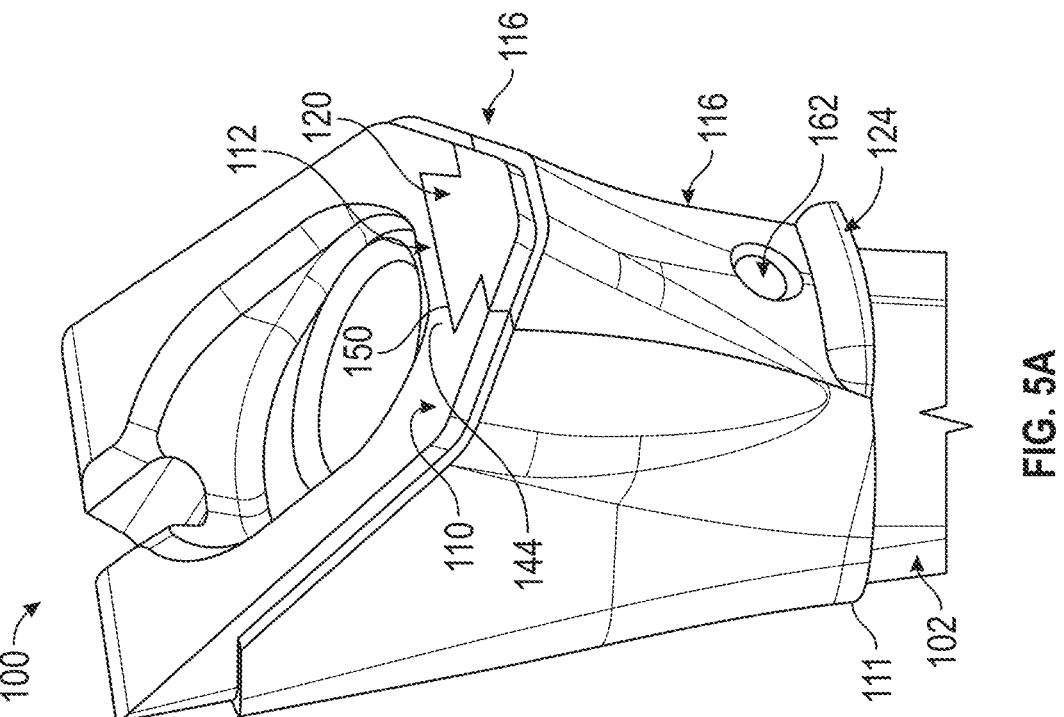
FIG. 5A illustrates an example stemmed modular implant system including a second accessory component, in accordance with one or more examples of the present disclosure.

FIG. 4A illustrates an example second accessory component 116 secured to a stem component 102, in accordance with one or more examples of the present disclosure. FIG. 4B illustrates an example second accessory component 116 of a stemmed modular implant system 100, in accordance with one or more embodiments of the present disclosure. FIG. 5A illustrates an example stemmed modular implant system 100 including a second accessory component 116, in accordance with one or more examples of the present disclosure. FIG. 5B illustrates an example second accessory component 116, in accordance with one or more examples of the present disclosure. In FIG. 4A, the proximal humerus 128 is shown with a lesser, relative to FIG. 2A, portion of the metaphysis 133 within the medial portion 129 remaining. Also shown in FIG. 4A is a first axis A1 and a third axis A3. FIGS. 3A-5B are discussed below concurrently.

In some examples, the proximal humerus 128 can define a second bone surface 154 (FIG. 4A). The second bone surface 154 can be an uppermost surface of the medial portion 129, such as extending laterally between the outer bone surface 134 (FIG. 4A) and the stem component 102 (FIGS. 4A & 5A). As such, the second bone surface 154 can be generally representative of, and depend on, the extent of bone loss or resorption of, or whether one or more fractures are present within, the metaphysis 133 or the diaphysis 135 within medial portion 129 of the proximal humerus 128. The lateral portion 138 (FIGS. 4B & 5B) of the second accessory component 116, and, in some examples, the third accessory component 118 (FIGS. 6A-7B), can include a first outer surface 156 (FIGS. 4B & 5B) and a second outer surface 158. The first outer surface 156 and the second outer surface 158 can form opposite upper and lower portions or segments of the second accessory component 116 and, in some examples, the third accessory component 118.

The second outer surface 158 can extend between the first pair of contacting surfaces 146 (FIGS. 2B & 3B) of the medial portion 136 (FIGS. 4B & 5B) and the first outer surface 156. The second outer surface 158 can define the projection 124. The projection 124 can generally be a portion or segment of the second accessory component 116 at least partially formed by the second outer surface 158, such as extending distally outward from the medial portion 136 by a distance greater than a distance the first outer surface 156 extend distally outward from the medial portion 136. The projection 124 can form various three-dimensional shapes, such as including, but not limited to, an ellipsoidal, semi-hemispherical, or generally elongated shape. In some examples, the stemmed modular implant system 100 can include a fastener 159 (FIG. 4B). In such examples, the second accessory component 116, or the first accessory component 114 (FIGS. 1 and 2A-3B) or the third accessory component 118 (FIGS. 1 & 6A-7B), can define a coupling bore 162 (FIGS. 3B, 4A-4B, & 5A-5B).

The fastener 159 can be, for example, but not limited to, a threaded fastener defining a first series of threads 164 (FIG. 3B). The coupling bore 162 can be a cylindrical bore extending through the medial portion 136 and the lateral portion 138. The coupling bore 162 can define a third axis A3. The coupling bore 162 can extend at various angles relative to the first portion 106 (FIG. 2A) of the stem component 102 (FIGS. 4A & 5A). For example, an angle β (FIG. 4A) can be the angle formed at an intersection of the first axis A1 defined by the first portion 106 and the third axis A3 defined by the coupling bore 160. The angle β can measure between about, but not limited to, 40 degrees to about 90 degrees. In one example, such as shown in FIG. 2A, the angle β can be about 45 degrees.

The coupling bore 162 can be adapted to receive the fastener 159. For example, the coupling bore 162 can be sized and shaped to receive a portion or length of the fastener 159 there through; and can define a second series of threads 166 (FIG. 4A). During assembly of the stemmed modular implant system 100, the first end surface 111 (FIGS. 4A & 5A) of the mounting boss 110 (FIGS. 4A & 5A) and the second end surface 121 of the medial portion 136 can be positioned flush with one another, or the second end surface 121 of the medial portion 136 can be positioned beyond or below the first end surface 111, to cause projection 124 to engage the second bone surface 154 (FIGS. 4A & 6A) and the coupling bore 162 to be positioned orthogonally to the first contacting surface 144 (FIG. 4A & FIG. 5B). Next, the fastener 159 can be inserted into, and rotated within, the coupling bore 162 to cause the first series of threads 164 to rotate within the second series of threads 166 to drive the fastener 159 into contact with the first contacting surface 144 of the stem component 102 to, in turn, cause fastener 159 to compressively clamp the second accessory component 116 against the stem component 102 and thereby maintain pressure on the second bone surface 154.

In some examples, the lateral portion 138 of the second accessory component 116 can be based on a statistical bone model representing, for example, a calculated average size and shape of the medial portion 129 of the proximal humerus 128 or a proximal femur after an amount of bone loss or resorption thereof, or a calculated average size and shape of the second bone surface 154, of a plurality of different patients. For example, the size and shape of the projection 124 or the second outer surface 158 of the lateral portion 138, or other parameters or characteristics of the second accessory component 116, can be configured based on a statistical bone model. A statistical bone model can be generated, for example, from imaging data including, but not limited to, CT, X-ray, or Magnetic Resonance Imaging data. In one example, the Zimmer Biomet ZiBRA Bone Resection Atlas (hereinafter the "ZiBRA Atlas"), which includes imaging data representing aggregated bone morphology from a diverse global population, can be used to create such a statistical bone model.

In some examples, the stemmed modular implant system 100 can include a plurality of second accessory components, such as, but not limited to, two, three, four, or five uniquely configured second accessory components to thereby form a standardized range of different shapes and sizes for the projection 124 or the second outer surface 158. This can enable a surgeon to conveniently select the second accessory component 116 therefrom based on one or more physical characteristics of patient's bone, such as the natural size and shape of the medial portion 129, an amount of the metaphysis 133 or the diaphysis 135 (FIG. 3A) remaining within the medial portion 129 after an amount of bone loss or resorption thereof, or the size and shape of the second bone surface 154. In a further example, the lateral portion 138 of the second accessory component 116 can be based on imaging data collected from an individual patient, such as to help enable the projection 124 or the second bone surface 154 engage abnormal humeral geometry falling outside a range of geometry a plurality of first accessory components is sized and shaped to engage. In such an example, it can be appreciated that the lateral portion 138 of the second accessory component 116 can be configured and manufactured specifically for the individual patient.

In some examples, the second accessory component 116 can include a porous surface 168 (FIG. 2B). For example, a portion, or all, of a surface area of the projection 124 or the second outer surface 158 can generally be a textured or a patterned three-dimensional structure adapted to help facilitate post-operative bone ingrowth and vascularization. In one example, the porous surface 168 can be realized using Zimmer Biomet OsseoTi® Porous Metal Technology, which uses human CT imaging data in combination with 3D printing technology to build a structure that mimics the architecture of human cancellous bone. In other examples, the porous surface 168 can be realized using Zimmer Biomet Proximal PPS® Porous Plasma Spray.

The second accessory component 116 can be adapted for and selected by a surgeon in secondary, such as revision, arthroplasties where or up to about 100 percent, of the metaphysis 133 within the medial portion 129 remains. For example, the projection 124 can be sized and shaped to engage both cancellous and cortical bone of the metaphysis 133 or the diaphysis 135 within the medial portion 129 by contacting and engaging cancellous bone forming the second bone surface 154 and cortical bone forming the outer bone surface 134 (FIG. 3A), In view of the above, when the stem component 102 and the second accessory component 116 are inserted into the proximal humerus 128, the projection 124 can engage a relatively large remaining surface area of both cancellous and cortical bone of the medial portion 129. As such, the second accessory component 116 can enable the stem component 102 to effectively transfer stress forces generated during normal joint movement into the medial portion 129 to prevent stress-shielding thereof and the periprosthetic bone loss or resorption associated therewith, such as irrespective of an amount of the degradation or decay of the medial portion 129.

Figures 6A, 6B:
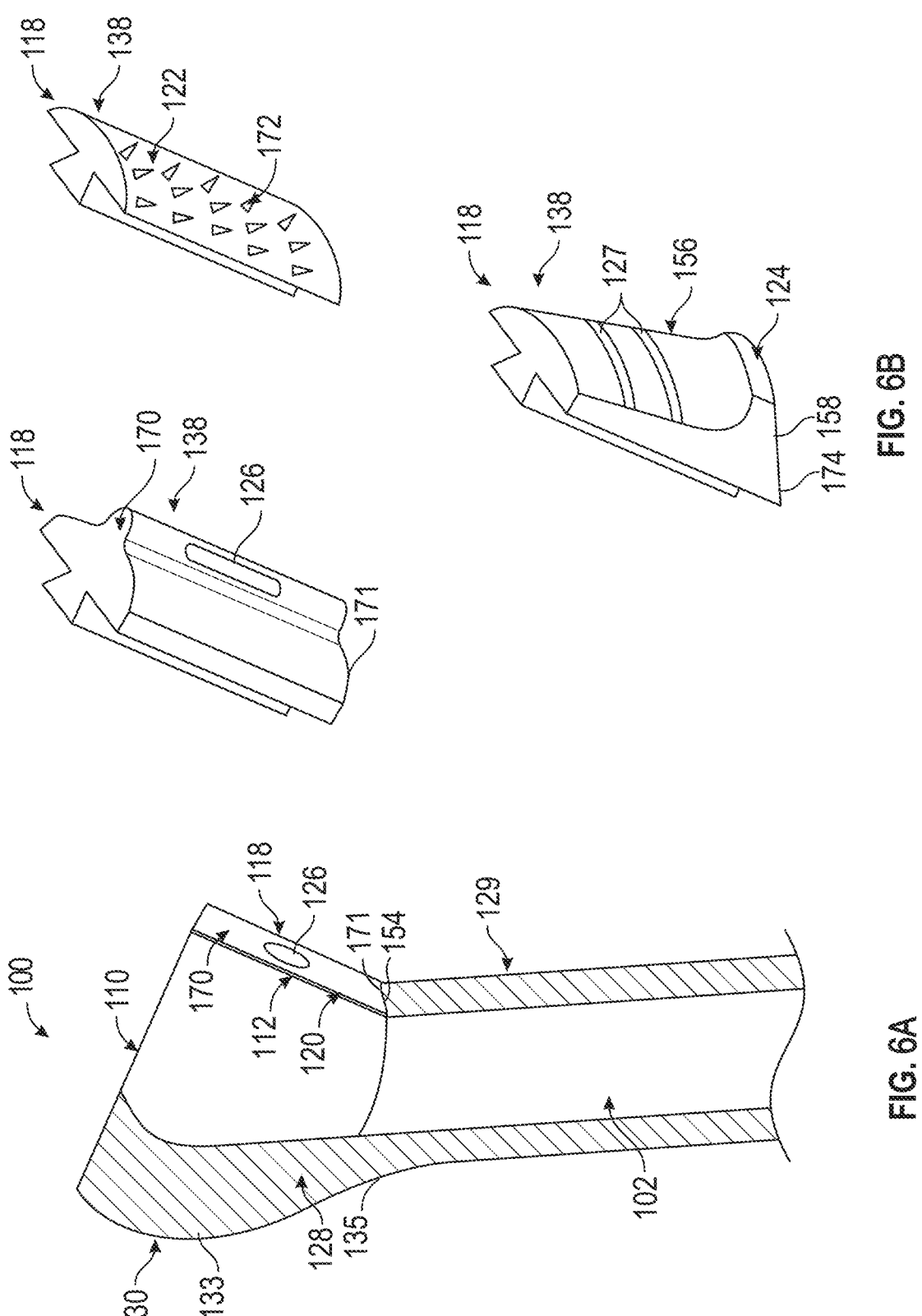
FIG. 6A illustrates a cross-section of an example stemmed modular implant system received within a proximal humerus.
FIG. 6B illustrates three examples of a third accessory component, in accordance with one or more examples of the present disclosure.
Figure 7B:
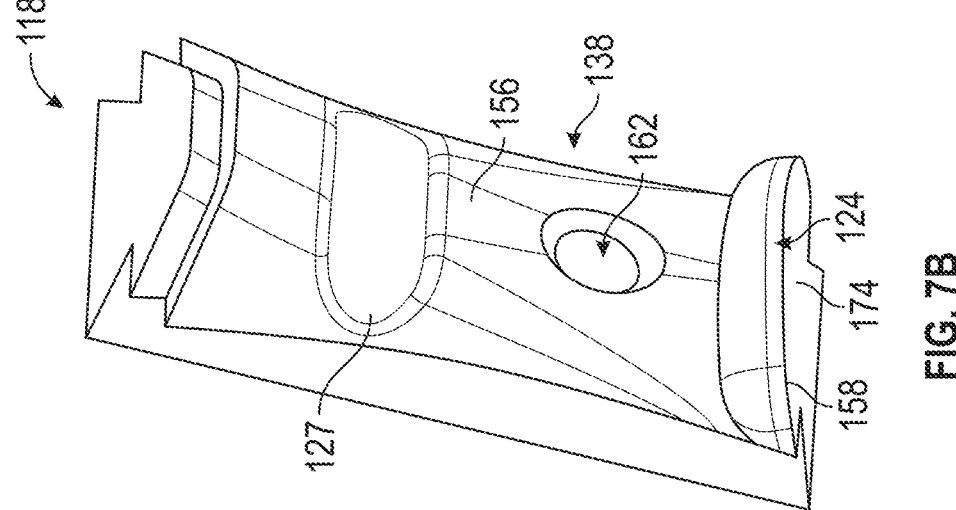
FIG. 7B illustrates an example stemmed modular implant system including a third accessory component, in accordance with one or more examples of the present disclosure.
Figure 7A:
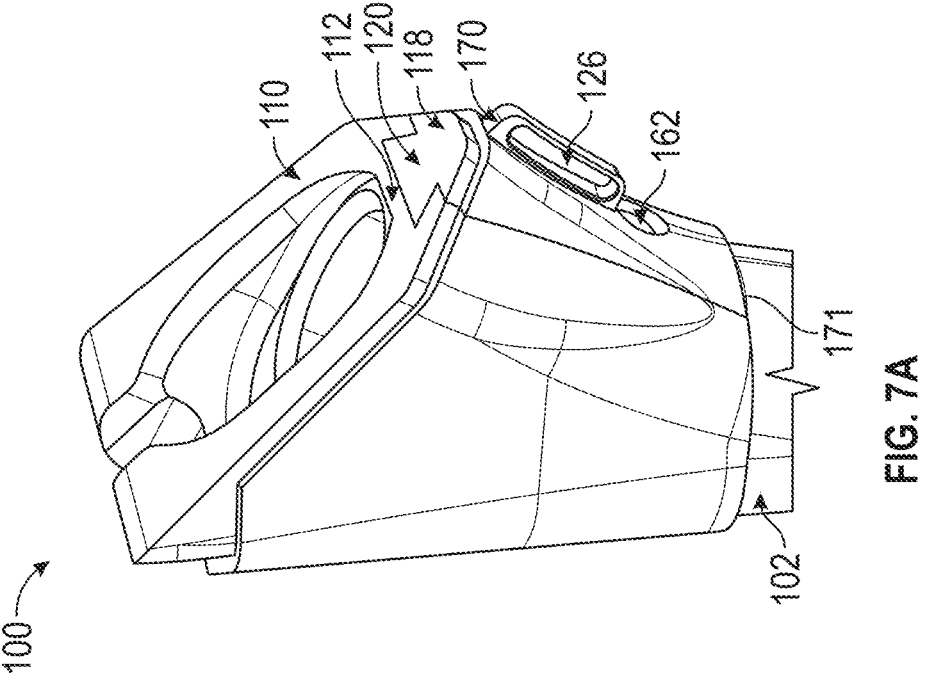
FIG. 7A illustrates an example stemmed modular implant system including a third accessory component, in accordance with one or more examples of the present disclosure.

FIG. 6A illustrates a cross-section of an example stemmed modular implant system 100 received within a proximal humerus 128. FIG. 6B illustrates three examples of a third accessory component 118, in accordance with one or more examples of the present disclosure. FIG. 7A illustrates an example stemmed modular implant system 100 including a third accessory component 118, in accordance with one or more examples of the present disclosure. FIG. 7B illustrates an example third accessory component 118, in accordance with one or more examples of the present disclosure. FIGS. 6A-7B are discussed below concurrently. In FIG. 7A, the proximal humerus 128 is shown with a lesser, relative to FIG. 2A, portion of the metaphysis 133 within the medial portion 129 remaining.

In some examples, the lateral portion 138 (FIGS. 6B & 7B) can include one or more fins 170 (FIGS. 6A-6B & 7A). In one example, such as shown in FIG. 4B, the one or more fins 170 can include a single fin. In another example, the one or more fins 170 can two, three, or four individual fins located equidistantly or non-equidistantly relative to on another in a radial arrangement about the lateral portion 138. Additionally, in some such examples, the third accessory component 118 can include a lower end surface 171. The lower end surface 171 can be generally similar to the projection 124 (FIG. 4A-5B) or the second outer surface 158 (FIGS. 4A-4B & 5B), at least in that the lower end surface 171 can be adapted to contact and engage the second bone surface 154 (FIG. 6A) of the proximal humerus 128.

Each fin of the one or more fins 170 (FIGS. 6A-6B & 7A) can define at least one aperture 126. In some examples, such as shown in FIG. 4B, the at least one aperture 126 can include a single aperture. In other examples, the at least one aperture 126 can include various numbers of individual apertures, such as between, but not limited to, about five individual apertures to about fifteen individual apertures spaced laterally apart, or otherwise distributed equidistantly or non-equidistantly across, each fin of the one or more fins 170. Each aperture of the at least one aperture 126 can extend into, or through, the one or more fins 170.

Each aperture of the at least one aperture 126 be sized and shaped to enable a wide variety of commercially available sutures to be passed there through, or a suture anchor to be received therein, to prevent movement of the suture or the suture anchor relative the first axis A1 (FIGS. 2A & 4A). Such a suture can be, for example, but not limited to, a Maxbraid® or Trulink® suture, or Broadband® Tape, available from Zimmer Biomet; and such a suture anchor can be, for example, but not limited to, a JuggerKnot®, SureLock®, or Quattro X® suture anchor available from Zimmer Biomet; and such a suture anchor can be, for example, but not limited to, a JuggerKnot®, SureLock®, or Quattro X® suture anchor available from Zimmer Biomet.

In other examples, the third accessory component 118 can include the projection 124 and the second outer surface 158. In such examples, the third accessory component 118 can include the one or more grooves 127 (FIGS. 6B & 7B). The one or more grooves 127 can include various numbers of individual grooves, such as between, but not limited to, about one individual groove to about four individual apertures spaced vertically apart, and extending parallel or non-parallel to each other, about the first outer surface 156. Each groove of the one or more grooves 127 can be a recess or a slot extending inwardly into, or inset within the third accessory component 118 relative to, the first outer surface 156 (FIGS. 6B & 7B).

Each groove of the one or more grooves 127 can be sized and shaped to enable a portion or a length of a wide variety of commercially available sutures to be received therein to prevent movement of such a suture relative the first axis A1. Such a suture can be, for example, but not limited to, a Maxbraid® or Trulink® suture, or Broadband® Tape, available from Zimmer Biomet; and such a suture anchor can be, for example, but not limited to, a JuggerKnot®, SureLock®, or Quattro X® suture anchor available from Zimmer Biomet; and such a suture anchor can be, for example, but not limited to, a JuggerKnot®, SureLock®, or Quattro X® suture anchor available from Zimmer Biomet.

In further examples, the third accessory component 118 can include the outer surface 122 (FIG. 6B). In such examples, the lateral portion 138 of the third accessory component 118 can include a plurality of radial protrusions 172 (FIG. 6B). Each protrusion of the plurality of radial protrusions 172 can be a spike or a pointed projection, such as forming a conical or a pyramidal shape, extending radially, distally, or otherwise outwardly from the outer surface 122. The plurality of radial protrusions 172 can include various numbers of individual protrusions, such as between, but not limited to, about ten to about one hundred individual protrusions distributed about the outer surface 122. Each protrusion of the plurality of radial protrusions 172 can be sized and shaped to help penetrate cancellous bone of one or more bone fragments of the medial portion 129 of the proximal humerus 128 to prevent movement of the one or more bone fragments relative the first axis A1, such as in addition to one or more sutures extending through, or wrapping around, the one or more bone fragments.

In some examples, the lateral portion 138 of the third accessory component 118 can be based on a statistical bone model representing, for example, a calculated average size and shape of one or more displaced fractures (e.g., bone fragments), such as one, two, or three displaced fractures, or a calculated average size and shape of a proximal humerus or proximal femur before or after an amount of bone loss or resorption, of a plurality of different patients. For example, the size and shape of the one or more fins 170 or the lower end surface 171, the number of individual fins the one or more fins 170 includes, the shape, position, or orientation of the at least one aperture 126 or the one or more grooves 127, the number of individual apertures of the at least one aperture 126 or the number of individual grooves of the one or more grooves 127, the shape, position, or orientation of the plurality of radial protrusions 172 or the outer surface 122, or the size, shape, and number of individual protrusions the plurality of radial protrusions 172 includes, or other parameters or characteristics of the lateral portion 138 of the third accessory component 118, can be configured based on a statistical bone model. A statistical bone model can be generated, for example, from imaging data including, but not limited to, CT, X-ray, or Magnetic Resonance Imaging data. In one example, the Zimmer Biomet ZiBRA Bone Resection Atlas (hereinafter the "ZiBRA Atlas"), which includes imaging data representing aggregated bone morphology from a diverse global population, can be used to create such a statistical bone model.

In some examples, the stemmed modular implant system 100 can include a plurality of third accessory components, such as, but not limited to, two, three, four, or five uniquely configured third accessory components to thereby form a standardized range of different shapes and sizes for the lateral portion 138 of the third accessory component 118, and standardized range of different arrangements or configurations for the one or more fins 170, the lower end surface 171, the at least one aperture 126, the one or more grooves 127, the second outer surface 158 or the projection 124, the plurality of radial protrusions 172, or the outer surface 122.

This can enable a surgeon to conveniently select the third accessory component 118 therefrom based on one or more physical characteristics of a patient's bone, such as the size, shape, and number of bone fragments of the medial portion 129 of the proximal humerus 128, an amount of the metaphysis 133 (FIG. 6A) or the diaphysis 135 (FIG. 6A) remaining within the medial portion 129, or the size and shape of the medial portion 129 after an amount of bone resorption or decay thereof. In a further example, the lateral portion 138 of the third accessory component 118 can be based on imaging data collected from an individual patient, such as to help enable the lateral portion 138 engage abnormal humeral geometry falling outside a range of geometry a plurality of first accessory components is sized and shaped to engage. In such an example, it can be appreciated that the lateral portion 138 of the third accessory component 118 can be configured and manufactured specifically for the individual patient.

In some examples, the third accessory component 118 can include a porous surface 174 (FIGS. 6B & 7B). For example, a portion, or all, of a surface area of projection 124, can include the porous surface 174. The porous surface 174 can generally be a textured or a patterned three-dimensional structure adapted to help facilitate post-operative bone ingrowth and vascularization. In one example, the porous surface 174 can be realized using Zimmer Biomet OsseoTi® Porous Metal Technology, which uses human CT imaging data in combination with 3D printing technology to build a structure that mimics the architecture of human cancellous bone. In other examples, the porous surface 174 can be realized using Zimmer Biomet Proximal PPS® Porous Plasma Spray.

In any of the above examples, the first accessory component 114 (FIGS. 1 & 2A-3B), the second accessory component 116 (FIGS. 1 & 4A-5B), or the third accessory component 118, can be made from a various materials, such as, but not limited to, ceramics, metals such as stainless steel, titanium, or other metal alloys, such as including cobalt or chromium, through three-dimensional printing, metallic molding, machining, additive manufacturing, or other manufacturing techniques.

The third accessory component 118 can be adapted for and selected by a surgeon in secondary, such as fracture correction, arthroplasties where one or more displaced or non-displaced bone fragments of a patient's bone are present. For example, a surgeon can utilize any of the one or more fins 170, the at least one aperture 126, the one or more grooves 127, or the plurality of radial protrusions 172, in securing one or more displaced bone fragments to the stem component 102 using sutures or suture anchors to restore natural humeral or femoral geometry or contacting and engage the second bone surface 154. In some such examples, such during a fracture correction arthroplasty where the medial portion 129 is missing, a surgeon can utilize the at least one aperture 126 or the one or more grooves 127 in suturing or otherwise attaching a greater tuberosity and other bone fragments to one another and to the third accessory component 118. In other examples, such as during a fracture correction arthroplasty where some or all of the medial portion 129 remains, a surgeon can utilize the plurality of radial protrusions 172 in securing a lesser tuberosity or other bone fragments to one another and to the third accessory component 118.

Moreover, in some examples, a surgeon can engage the second bone surface 154 with the lower end surface 171, or the second outer surface 158 or the projection 124, to maintain a downward compression force or tension force on second bone surface 154. In view of the above, the third accessory component 118 can provide a surgeon with a wide variety of different customization options to help accurately reconstruct natural humeral geometry, and thereby help restore joint functionality, in secondary, or fracture correction arthroplasties; and, the third accessory component 118 can enable the stem component 102 to effectively transfer stress forces generated during normal joint movement into the medial portion 129 to prevent stress-shielding thereof and the periprosthetic bone loss or resorption associated therewith, such as irrespective of an amount of the displaced bone fractures of, or non-displaced bone fractures within, the medial portion 129.

FIG. 8 illustrates a method 200 of adapting a modular implant system to a patient. The steps or operations of the method 200 are illustrated in a particular order for convenience and clarity; many of the discussed operations can be performed by multiple different actors, devices, or systems.

It is understood that subsets of the operations discussed in the method 200 can be attributable to a single actor, device, or system and can be considered a separate standalone process or method.

The method 200 can begin with operation 202. The operation 202 can include selecting a stem component adapted to be anchored within a medullary canal of a bone of the patient. For example, a surgeon can select the stem component from a plurality of stem components based on a natural size and shape of the patient's proximal humerus or proximal femur, such as including a length or diameter of a medullary canal or diaphysis thereof.

The method 200 can include operation 204. The operation 204 can include selecting an accessory component from a plurality of accessory components based on a physical characteristic of the bone of the patient. For example, a surgeon can select the accessory component from the plurality of accessory components by selecting one of a first accessory component adapted for a primary shoulder arthroplasty, a second accessory component adapted for a secondary shoulder arthroplasty, or a third accessory component adapted for a secondary shoulder arthroplasty based on a natural size and shape of a medial portion of a patient's proximal humerus or femur, an amount of an epiphysis, metaphysis, or diaphysis remaining within the medial portion, the size and shape of a first bone surface defined within the medial portion, the size and shape of a second bone surface defined by the medial portion, or whether where one or more displaced bone fragments of the medial portion are present.

The method 200 can include operation 206. The operation 206 can include securing the accessory component to the stem component. For example, a surgeon can first align an outer coupling surface of the accessory component with an inner coupling surface of the stem component. The surgeon can then apply an axial downward force to the accessory component to cause the outer coupling surface to slide along the inner coupling surface toward a first portion of the stem component, such as until a first end surface of the stem component is aligned with a second end surface of the accessory component.

In some examples, the operation 206 can include engaging an inner coupling surface of stem component with an outer coupling surface of the accessory component to form a dovetail joint there between. For example, the surgeon can apply an axial downward force to the accessory component to cause a first pair of contacting surfaces, a second pair of contacting surface, and a first contacting surface of the stem component to slide along a third pair of contacting surface, a fourth pair of contacting surface, and a second contacting surface of the accessory component, such as until a first end surface of the stem component is aligned with a second end surface of the accessory component.

While the above description of the modular implant system is generally discussed with reference to a medial portion of a proximal humerus or femur, it is to be appreciated that the stemmed modular implant system 100 of the present disclosure, and any of its associated benefits, is also applicable to the lateral portion 130 of the proximal humerus 128. For example, the mounting boss 110 can include a second coupling surface, such as positioned 180 degrees offset about the outer stem surface 125, and the plurality of accessory component 104 (FIG. 1) can be adapted to engage cancellous or cortical bone of the lateral portion 130 to prevent While the above description of the modular implant system is generally discussed with reference to a humerus in the context of shoulder arthroplasties, it to be appreciated that the stemmed modular implant system 100 of the present disclosure, and any of its associated benefits, is also applicable to other ball and socket type joints, such as, but not limited to, the femur in the context of hip arthroplasties, or one or more bones of a wrist or elbow joint.

The foregoing systems and devices, etc. are merely illustrative of the components, interconnections, communications, functions, etc. that can be employed in carrying out examples in accordance with this disclosure. Different types and combinations of sensor or other portable electronics devices, computers including clients and servers, implants, and other systems and devices can be employed in examples according to this disclosure.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided.

Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein. In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72 (b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure.

This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

EXAMPLES

The following, non-limiting examples, detail certain aspects of the present subject matter to solve the challenges and provide the benefits discussed herein, among others.

Example 1 is a stemmed implant system, comprising: a stem component including: a first portion adapted to be anchored within a medullary canal of a bone; a second portion including a mounting boss defining an inner coupling surface; and an accessory component defining an outer coupling surface, the outer coupling surface adapted to engage the inner coupling surface of the mounting boss to secure the accessory component to the stem component.

In Example 2, the subject matter of Example 1 includes, wherein the outer coupling surface of the accessory component and the inner coupling surface of the mounting boss are adapted to engage each other via a press fit or a taper fit.

In Example 3, the subject matter of Examples 1-2 includes, wherein the outer coupling surface of the accessory component and the inner coupling surface of the mounting boss form a dovetail joint.

In Example 4, the subject matter of Examples 1-3 includes, wherein the accessory component includes a medial portion defining the outer coupling surface and a lateral portion including an outer surface adapted to engage the bone and fill an anatomical void within a patient.

In Example 5, the subject matter of Example 4 includes, wherein the outer surface of the lateral portion forms a curved or semi-annular shape.

In Example 6, the subject matter of Example 5 includes, wherein the outer surface of the lateral portion includes a plurality of radial projections adapted to engage a first bone surface of the bone.

In Example 7, the subject matter of Examples 5-6 includes, wherein the lateral portion includes a porous surface.

In Example 8, the subject matter of Examples 4-7 includes, wherein the lateral portion of the accessory component includes a projection adapted to engage a second surface of the bone.

In Example 9, the subject matter of Example 8 includes, wherein the lateral portion of the accessory component defines one or more grooves each adapted to receive a portion of a suture.

In Example 10, the subject matter of Examples 4-9 includes, wherein the lateral portion of the accessory component includes one or more fins defining at least one aperture extending there through, each of the one or more apertures adapted to receive a portion of a suture there though or a suture anchor therein.

In Example 11, the subject matter of Examples 4-10 includes, wherein: the stemmed implant system includes a fastener; and the accessory component defines a coupling bore adapted to receive the fastener, the coupling bore extending through the medial portion and the lateral portion.

Example 12 is a stemmed implant system, comprising: a stem component including: a first portion adapted to be anchored within a medullary canal of a bone; a second portion including a mounting boss defining an inner coupling surface; and a plurality of accessory components each uniquely sized and shaped relative to other accessory components of the plurality of accessory components, wherein each accessory component of the plurality of accessory components includes: a medial portion defining an outer coupling surface adapted to engage the inner coupling surface of the mounting boss to secure an accessory component to the stem component; and a lateral portion adapted to engage the bone and fill an anatomical void within a patient.

In Example 13, the subject matter of Example 12 includes, wherein the plurality of accessory components includes at least one first accessory component adapted for a primary shoulder arthroplasty and at least one second accessory component adapted for a secondary shoulder arthroplasty.

In Example 14, the subject matter of Example 13 includes, wherein the at least one first accessory component includes an outer surface adapted to engage a first surface of the bone, the first surface formed by cancellous bone; and the at least one second accessory component includes a projection adapted to engage a second surface of the bone, the second surface formed by cancellous and cortical bone.

In Example 15, the subject matter of Example 14 includes, wherein the plurality of accessory components at least one third accessory component adapted for a shoulder fracture correction arthroplasty.

In Example 16, the subject matter of Example 15 includes, wherein the at least one third accessory component includes one or more fins defining at least one aperture extending there through, the at least one aperture adapted to receive a portion of a suture there through or a suture anchor therein.

Example 17 is a method of adapting a stemmed implant system to a patient, the method comprising: selecting a stem component adapted to be anchored within a medullary canal of a bone of the patient; selecting an accessory component from a plurality of accessory components based on a physical characteristic of the bone of the patient; and securing the accessory component to the stem component.

In Example 18, the subject matter of Example 17 includes, wherein selecting the accessory component from the plurality of accessory components includes selecting the accessory component based on an amount of the bone remaining or a number of bone fragments of the bone.

In Example 19, the subject matter of Examples 17-18 includes, wherein selecting the accessory component from the plurality of accessory components includes selecting a first accessory component from a plurality of first accessory components adapted for a primary shoulder arthroplasty or selecting a second accessory component from a plurality of second accessory components adapted for a secondary shoulder arthroplasty.

In Example 20, the subject matter of Examples 17-19 includes, wherein securing the accessory component to the stem component includes slidably engaging an inner coupling surface of stem component with an outer coupling surface of the accessory component to form a dovetail joint there between.

Example 21 is at least one machine-readable medium including instructions that, when executed by processing circuitry, cause the processing circuitry to perform operations to implement of any of Examples 1-20.

Example 22 is an apparatus comprising means to implement of any of Examples 1-20.

Example 23 is a system to implement of any of Examples 1-20.

Example 24 is a method to implement of any of Examples 1-20.

What is claimed is:

1. A stemmed implant system, comprising:
a stem component including:
a first portion adapted to be anchored within a medullary canal of a bone; and
a second portion including a mounting boss defining an inner coupling surface;
a fastener; and
an accessory component defining an outer coupling surface, the outer coupling surface adapted to engage the inner coupling surface of the mounting boss to secure the accessory component to the stem component, wherein:
the accessory component includes a medial portion defining the outer coupling surface and a lateral portion including an outer surface adapted to engage the bone and fill an anatomical void within a patient;
the outer coupling surface and the inner coupling surface form a dovetail joint; and
the accessory component defines a coupling bore adapted to receive the fastener, the coupling bore extending through the medial portion and the lateral portion and intersecting the dovetail joint;
wherein the mounting boss defines part of an outer circumference of the second portion, the second portion defining an upper most surface where the inner coupling surface extends transversely from the upper most surface to an upper portion of the first portion, and wherein the fastener is configured to be inserted through the coupling bore from the lateral portion toward the medial portion.

2. The stemmed implant system of claim 1, wherein the outer coupling surface of the accessory component and the inner coupling surface of the mounting boss are adapted to engage each other via a press fit or a taper fit.

3. The stemmed implant system of claim 1, wherein the outer surface of the lateral portion forms a curved or semi-annular shape.

4. The stemmed implant system of claim 3, wherein the outer surface of the lateral portion includes a plurality of radial projections adapted to engage a first bone surface of the bone.

5. The stemmed implant system of claim 3, wherein the lateral portion includes a porous surface.

6. The stemmed implant system of claim 1, wherein the lateral portion of the accessory component includes a projection adapted to engage a second surface of the bone.

7. The stemmed implant system of claim 6, wherein the lateral portion of the accessory component defines one or more grooves each adapted to receive a portion of a suture.

8. The stemmed implant system of claim 1, wherein the lateral portion of the accessory component includes one or more fins defining at least one aperture extending there through, the at least one aperture adapted to receive a portion of a suture there through or a suture anchor therein.

9. A stemmed implant system, comprising:
a stem component including:

a first portion adapted to be anchored within a medullary canal of a bone; and a second portion including a mounting boss defining an inner coupling surface;

a fastener; and a plurality of accessory components each uniquely sized and shaped relative to other accessory components of the plurality of accessory components, wherein each accessory component of the plurality of accessory components includes:

a medial portion defining an outer coupling surface adapted to engage the inner coupling surface of the mounting boss to secure an accessory component to the stem component;

a lateral portion adapted to engage the bone and fill an anatomical void within a patient;

wherein the outer coupling surface and the inner coupling surface form a dovetail joint when assembled; and a coupling bore adapted to receive the fastener, the coupling bore extending through the medial portion and the lateral portion and intersecting the dovetail joint;

wherein the mounting boss defines part of an outer circumference of the second portion, the second portion defining an upper most surface where the inner coupling surface extends transversely from the upper most surface to an upper portion of the first portion, and wherein the fastener is configured to be inserted through the coupling bore from the lateral portion toward the medial portion.

10. The stemmed implant system of claim 9, wherein the plurality of accessory components includes at least one first accessory component adapted for a primary shoulder arthroplasty and at least one second accessory component adapted for a secondary shoulder arthroplasty.

11. The stemmed implant system of claim 10, wherein the at least one first accessory component includes an outer surface adapted to engage a first surface of the bone, the first surface formed by cancellous bone; and the at least one second accessory component includes a projection adapted to engage a second surface of the bone, the second surface formed by cancellous and cortical bone.

12. The stemmed implant system of claim 11, wherein the plurality of accessory components at least one third accessory component adapted for a shoulder fracture correction arthroplasty.

13. The stemmed implant system of claim 12, wherein the at least one third accessory component includes one or more fins defining at least one aperture extending there through, the at least one aperture adapted to receive a portion of a suture therethrough or suture anchor therein.

14. A method of adapting a stemmed implant system to a patient, the method comprising:

selecting a stem component adapted to be anchored within a medullary canal of a bone of the patient, the stem component including:

a first portion adapted to be anchored within the medullary canal of the bone; and a second portion including a mounting boss defining an inner coupling surface;

wherein the mounting boss defines part of an outer circumference of the second portion, the second portion defining an upper most surface where the inner coupling surface extends transversely from the upper most surface to an upper portion of the first portion;

selecting an accessory component from a plurality of accessory components based on a physical characteristic of the bone of the patient; and securing the accessory component to the stem component, wherein securing the accessory component to the stem component includes slidably engaging an inner coupling surface of the stem component with an outer coupling surface of the accessory component to form a dovetail joint there between and inserting a fastener through a coupling bore of the accessory component that extends through the dovetail joint, the fastener insertable from a lateral portion of the accessory component toward a medial portion of the accessory component.

15. The method of claim 14, wherein selecting the accessory component from the plurality of accessory components includes selecting the accessory component based on an amount of the bone remaining or a number of bone fragments of the bone.

16. The method of claim 14, wherein selecting the accessory component from the plurality of accessory components includes selecting a first accessory component from a plurality of first accessory components adapted for a primary shoulder arthroplasty or selecting a second accessory component from a plurality of second accessory components adapted for secondary shoulder arthroplasty.

* * * * *